United States Patent [19]

Dube et al.

[11] 4,209,471
[45] Jun. 24, 1980

[54] PROCESS FOR THE PURIFICATION OF O,O-DI(LOWER)ALKYLDITHIOPHOSPHORIC ACIDS

[75] Inventors: James H. Dube, Mobile, Ala.; Ralph Miller, Pleasantville, N.Y.

[73] Assignee: Ciba-Geigy Corporation, Ardsley, N.Y.

[21] Appl. No.: 795,460

[22] Filed: May 10, 1977

[51] Int. Cl.$^2$ .............................................. C07F 9/165
[52] U.S. Cl. ................................................ 260/990
[58] Field of Search ................................ 260/990, 981

[56] References Cited

U.S. PATENT DOCUMENTS 2,335,511  11/1943  Havemann et al. ................. 260/990
3,573,293   3/1971  Wiese .

FOREIGN PATENT DOCUMENTS 1228528  4/1971  United Kingdom .

OTHER PUBLICATIONS

Kirk–Othmer, "Encyclopedia of Chemical Technology", p. 322.

Primary Examiner—Anton H. Sutto
Attorney, Agent, or Firm—Karl F. Jorda

[57] ABSTRACT

A liquid-liquid extraction method for recovering O,O-di(lower)alkyldithiophosphoric acid of increased purity from a crude mixture in which it is contained comprises intimately contacting said mixture with an acidic aqueous solution to form two liquid phases whereby the concentration of the thiophosphoric acid in the aqueous phase is increased; separating the two phases; contacting the aqueous phase with a stable, water-immiscible, volatile, organic solvent to form two liquid phases whereby the concentration of the thiophosphoric acid in the organic solvent is increased; separating the two phases; and vaporizing the organic solvent to recover high purity O,O-di(lower)alkyl dithiophosphoric acid.

7 Claims, 1 Drawing Figure

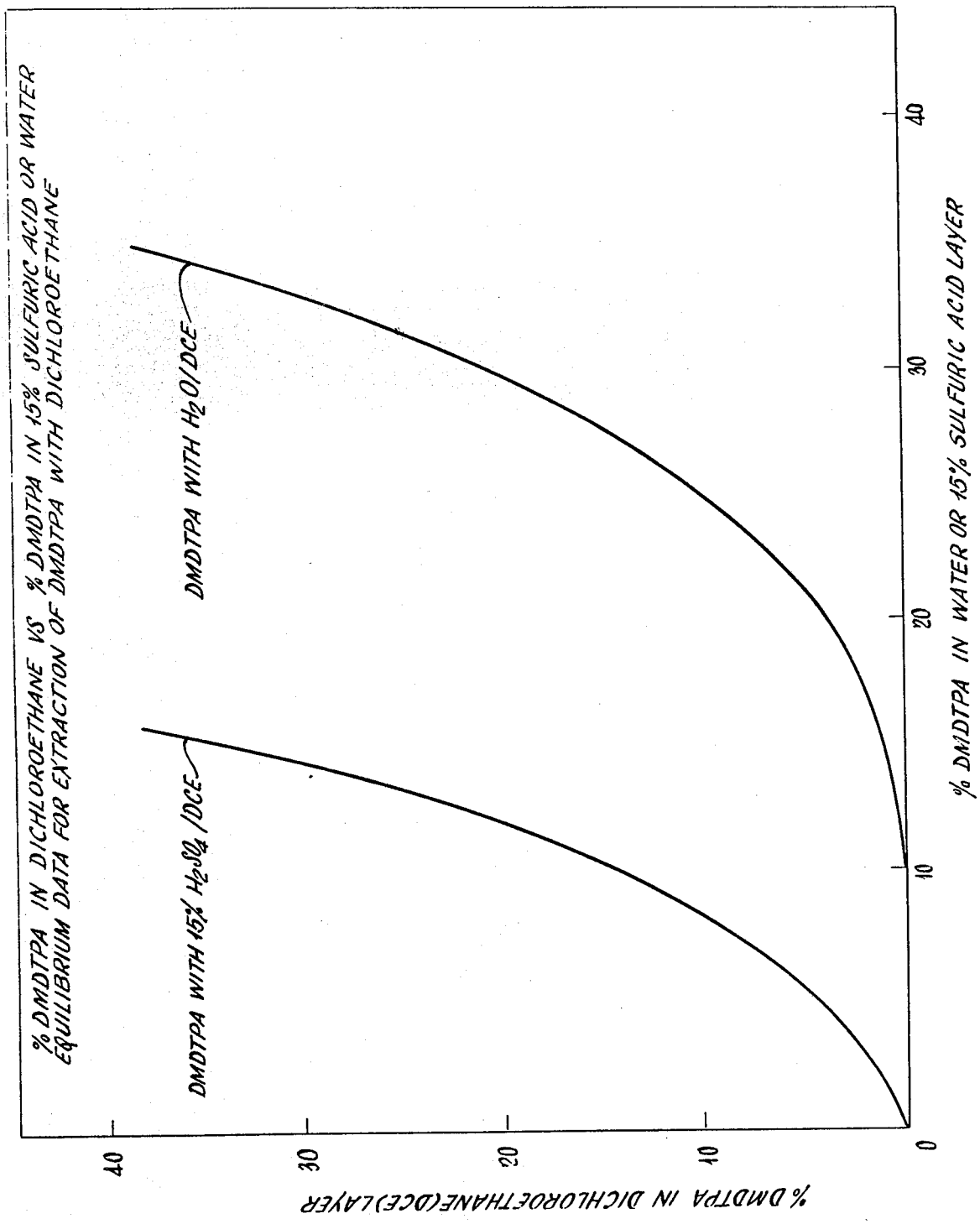

PROCESS FOR THE PURIFICATION OF O,O-DI(LOWER)ALKYLDITHIOPHOSPHORIC ACIDS

The present invention relates to a process for recovering O,O-di(lower)alkyldithiophosphoric acids and, more particularly, to a liquid-liquid extraction method for recovering high-purity O,O-di(lower)alkyldithiophosphoric acids.

O,O-Di(lower)alkyldithiophosphoric acids are especially useful as intermediates for the production of thiophosphoric acid derivatives of 1,3,4-thiadiazol-2-one or thione compounds as disclosed and claimed in U.S. Pat. No. 3,230,230 and, in particular, of O,O-dimethyl-S-[2-methoxy-1,3,4-thiadiazol-5(4H)-onyl-(4)-methyl]dithiophosphate (methidathion, SUPRACIDE), which has achieved commercial importance as an insecticide.

These O,O-di(lower)alkyldithiophosphoric acid intermediates are produced, in a well-known manner, by reacting phosphorus pentasulfide with four equivalents of a lower alkanol, in the absence or in the presence of a catalyst, e.g., ammonia in accordance with British Pat. No. 1,228,528 or an amine in accordance with U.S. Pat. No. 3,573,293. This reaction can be illustrated by the following reaction scheme:

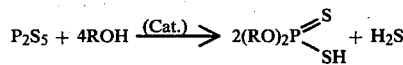

wherein R is lower alkyl of 1 to 3 carbon atoms.

Unfortunately, this reaction produces, even if a catalyst is used to improve product purity and quality, not only the desired O,O-di(lower)alkyldithiophosphoric acids (hereinafter "thio acids") but also several undesirable by-products or impurities, each in amounts of up to 5%, such as O,O-S-tri(lower)alkylphosphorothiolate [$(RO)_2P$-$(S)SCH_3$)], O,O,O-tri(lower)alkylphosphorothionate [$(RO)_2P$-$(O)SCH_3$], bis-[di(lower)alkoxyphosphoryl]sulfide [$(RO)_2P$-$(S)$-$S$-$P(S)(OR_2)$] and bis-[di(lower)alkoxyphosphino]sulfide [$(RO)_2P$-$S$-$P(OR_2)$].

This mixture of desired product (90% or less) and undesirable byproducts (10% or more) will be referred to hereinafter as "crude thio acid".

However, for conversion to the final thiophosphoric acid derivatives of 1,3,4-thiadiazol-2-thione compounds and in order to obtain this material of requisite purity and quality and to otherwise satisfy product specifications, the crude thio acid starting material has to be purified or upgraded before it can be employed in the above-mentioned conversion. Several standard methods are available for such purification or upgrading, such as, for instance, the "ammonium salt" method or various distillation techniques.

The "ammonium salt" method consists in precipitating out the ammonium salt of the thio acid from a solution of the crude material with anhydrous ammonia, filtering and reslurrying the ammonium salt in inorganic solvent, followed by reacidifying the ammonium salt with anhydrous hydrochloric acid and isolating the desired thio acid by solvent stripping. This method is fraught with several complications. Extensive fume control during the reaction is needed; especially during the ammonia and hydrochloric acid additions, and there are process effluent and raw materials handling and storage problems.

As regards distillation techniques, batch distillation and thin-film evaporation, for example, are known for purification of commercially available crude thio acids. These techniques also have serious shortcomings due, in particular, to the need for the maintenance of high vacuum during the distillation. These substances are thermally unstable. They decompose violently with rapid gas evolution when overheated. Thus, all of the above and other available purification methods and techniques leave something to be desired from the standpoint of safe, efficient and economical large-scale processing.

In the search for better and cheaper purification technology, it has now been found—and this forms the principal object of this invention—that by means of liquid-liquid extraction high-purity thio acid can be recovered from the commercially produced or available crude thio acid. This liquid-liquid extraction involves intimately contacting the crude thio acid with water or preferably a dilute aqueous acid to form two liquid phases whereby the concentration of the thio acid in the aqueous phase is increased, separating the two phases; contacting the aqueous phase with a stable, water-immiscible volatile organic solvent to form a system composed of two liquid phases whereby the concentration of the thio acid in the organic solvent is increased; separating the two phases; and vaporizing the organic solvent to recover high-purity thio acid.

This liquid-liquid extraction method reduces the potential safety hazards present in vacuum distillation of the thermally unstable thio acid, eliminates the need to first make the ammonium salt of the thio acid and then reacidify it and overcomes the complications and shortcomings incident to prior art and other available or accessible procedures. Furthermore, this extraction technique results in the recovery of high-purity product which carries over into the production therefrom of the desired insecticidal end product with low impurity content, facilitates the conversion to the insecticidal end product by the choice of a solvent which is useful in both the purification method and the conversion reactant, and permits the recovery and recycle of unextracted thio acid.

Furthermore, the liquid-liquid extraction method described herein is suitable for large-scale processing even though the thio acid at one stage of the process is dissolved in water or an aqueous acidic solution. The suitability of the process for large-scale processing is achieved by keeping the thio acid, the instability of which is well-known, dissolved in water or a dilute acid solution for only a short period of time and by keeping the temperature of the solution at ambient or lower temperatures.

In a first step of this extraction method the crude thio acid is intimately contacted with an aqueous extractant, preferably a dilute acid solution. The contacting is carried out at room temperature or below and for a sufficient time so as to establish equilibrium. The ratio of volume of aqueous extractant to volume of crude thio acid is about 2 to 1 or higher.

In selecting the aqueous extractant, it is advantageous to use an additive to water in order to alter the solubility of the thio acid and thereby facilitate the transfer of the thio acid from the aqueous extractant to the water-immiscilbe volatile solvent.

A suitable additive is an inorganic substance which is inert to the thio acid and reduces the solubility of the thio acid in water. Suitable additives include sulfuric and phosphoric acids and salts thereof, e.g., alkali metal salts which do not react with the thio acids.

The aqueous extractants mentioned above have solvent power for the pure thio acid but little or no solvent power for the other constituents of the crude thio acid mixture.

As a result of the above described mixing, two separable liquid phases result. The aqueous phase contains the water plus the bulk of the pure thio acid. The other liquid phase contains the impurities originally in the crude thio acid plus the remainder of the pure thio acid. The aqueous phase is then separated from the impurity phase by settling or centrifuging.

The separated aqueous phase is then intimately contacted, in a second step, with a stable, water-immiscible, volatile, organic solvent at ambient temperature or below until equilibrium is reached. Equilibrium is reached quickly. Once again, two separable liquid phases result. The thio acid originally contained in the aqueous phase is now divided between the two phases. The two phases are separated. The separated aqueous extractant is recycled to the first extraction step and the separated organic solvent phase is heated, preferably under vacuum to a temperature at which substantially all of the solvent vaporizes but none of the thio acid. Batch distillation or thin-film evaporation techniques can be employed. The vaporized solvent is condensed and recovered for recycling. Substantially pure thio acid is recovered from the still pot.

Suitable stable water-immiscible volatile organic solvents include chlorinated hydrocarbons, such as, in particular methylene chloride, dichloroethane, trichloroethane, chloroform, carbon tetrachloride etc., aromatic hydrocarbons, such as, in particular, benzene, toluene, xylene, etc., and ethers, provided they have a boiling point of less than 45° C. at 1 mm Hg and are immiscible with water.

This liquid-liquid extraction method has been described by way of batch operations but it can also be carried out, as is obvious to men skilled in the art, in a continuous fashion. The continuous method is preferred when large amounts have to be processed in which case thin film evaporation is used for thio acid isolation and recovery.

As shown by the data obtained in Example I it is not possible to obtain high yields of high assay DMDTPA by multiple batch extractions even when high ratios of organic solvent to water are employed.

It has been found that when the concentration of DMDTPA in water approaches 20% by weight, water exerts a much greater solvent power for the thio acid than the organic solvents employed in this invention. As a result, it is not economically feasible to extract DMDTPA from aqueous solutions containing less than about 20% of the thio acid.

When the solvent power of water for the thio acids is diminished by the above mentioned additives, it becomes possible to substantially extract all of the dissolved DMDTPA from modified solutions.

This finding is shown by the data portrayed by the curves in the attached FIGURE.

The points used to draw these curves were obtained as follows:

Initially a saturated solution of DMDTPA in water was prepared. A quantity of this solution was then placed into a separatory funnel along with a quantity of fresh solvent (1,2-dichloroethane). The two immiscible phases were shaken in the separatory funnel for several minutes then allowed to separate over a 10–15 minute period. The two layers were isolated. The concentration of DMDTPA was then determined in each phase. By varying the weight ratio of DMDTPA solution to fresh solvent charged to the separatory funnel sufficient data points were obtained to plot the equilibrium curve. For example, point A was obtained by agitating 40 g of solvent and 10 g of saturated aqueous DMDTPA solution (39%) in a separatory funnel. Following a phase split, the solvent layer analyzed 5.5% DMDTPA and the aqueous layer analyzed 21.8% DMDTPA. These analyses were plotted as point A.

The same procedure was followed to obtain a corresponding curve for the 15% sulfuric acid diluent. Comparison of the curves indicates the degree with which sulfuric acid influences the equilibrium curve. Based on this data more complete removal of DMDTPA from sulfuric acid diluent is possible than can be achieved if water alone is used. The possibility of DMDTPA hydrolysis upon prolonged storage of the aqueous stream leaving the second stage (dichloroethane) extraction column is therefore reduced when sulfuric acid is used as the diluent. This characteristic points out the advantage of using sulfuric acid as the solvent in the first step of the two step extraction process.

The following non-limitative examples serve to illustrate the inventive process further. Where not stated otherwise, parts and percentages are given by weight and the temperatures in degrees Centigrade. DMDTPA stands for O,O-dimethyldithiophosphoric acid.

EXAMPLE 1

Water Extraction of DMDTPA

To a 2-liter glass Erlenmeyer flask 557 grams of crude DMDTPA (85%) and 1000 grams of water were charged. The mixture was agitated vigorously for about 2 minutes. The mixture was transferred to a 3-liter separatory funnel and the two liquid phases allowed to separate. Within 5 minutes complete separation had taken place. The more dense, organic layer containing the bulk of the impurities was transferred to the original Erlenmeyer flask. The less dense, aqueous layer was transferred to a second Erlenmeyer flask.

Dichloroethane Extraction of DMDTPA/Water Phase

To the aqueous layer in the second Erlenmeyer flask, 1000 grams of 1,2-dichloroethane (hereinafter DCE) was added. The mixture was agitated vigorously and the mixture transferred to the 3-liter separatory funnel. After allowing the phases to separate, the more dense, DCE phase, was separated from the aqueous phase. The separated DCE phase was transferred to a storage container for later separation. The aqueous phase was returned to the Erlenmeyer flask, contacted with an additional 1000 grams of DCE, and the complete cycle repeated a total of 5 times. That is, a total of 5000 grams of DCE was used to extract the 1000 grams of water used to extract the DMDTPA from the original crude thio acid.

The solution of DMDTPA in DCE was then evaporated at a reduced pressure of 30 mm of Hg. The temperature was not allowed to exceed 40° C. The DCE-free residual DMDTPA had an assay of 96%.

The yield of high purity DMDTPA was about 50%. Most of the unrecovered DMDTPA was in the aqueous phase. A small amount was lost in the various manipulations.

EXAMPLE 2

Water (1300 g) was charged into 1000 g of DMDTPA (85%). The mixture was agitated vigorously for 5 minutes, transferred to a separatory funnel, and the layers were allowed to separate for 5 minutes.

The bottom organic layer was drained and discarded. The top aqueous layer was poured into an agitated reaction vessel.

To the aqueous layer 900 g of 1,2-dichloroethane was added. The mixture was agitated for 5 minutes and transferred to a separatory funnel where the layers were allowed to separate for 5 minutes.

The bottom organic layer was drained and transferred to a vacuum distillation apparatus. The top aqueous layer was discarded.

In the vacuum distillation system, the 1,2-dichloroethane was removed at 5 mm Hg and 25° C.

187.5 g of DMDTPA assaying 96.6% on a solvent-free basis was isolated.

EXAMPLE 3

There was charged 1500 gms of 15% $H_2SO_4$ into 1500 gms of 85% DMDTPA. The mixture was agitated vigorously for 5 minutes, transferred to a separatory funnel and the layers were allowed to separate for 15 minutes.

The bottom organic layer was drained and discarded. The top aqueous layer was poured into an agitated reaction vessel.

To the aqueous layer 1710 gms of 1,2-dichloroethane were added. The mixture was agitated for 15 minutes and transferred to a separatory funnel where the layers were allowed to separate for 5 minutes.

The bottom organic layer was drained and transferred to a vacuum distillation apparatus. The top aqueous layer was discarded.

In the vacuum distillation system, the 1,2-dichloroethane was removed at 5.0 mm Hg and 25° C.

190.0 gms of DMDTPA assaying 96.3% on a solvent-free basis was isolated.

The O,O-diethyl homolog of DMDTPA which after analogous conversion also yields an effective insecticidal compound can also be purified in an analogous fashion with analogous results.

The invention has been illustrated by way of a few preferred embodiments. It is to be understood, however, that such modifications and variations as would be obvious to persons skilled in the art are within the scope of the appended claims.

What is claimed is:

1. A method for recovering high-purity O,O-di(-lower)alkyldithiophosphoric acid from a crude thio acid mixture obtained from the reaction of phosphorous pentasulfide and four equivalents of a lower alkanol which comprises contacting said crude thio acid mixture with water or an acidic aqueous solution to form two liquid phases, said acidic aqueous solution containing an inorganic substance which is inert to the thio acid and reduces the solubility of the thio acid in water, separating the two phases, contacting the aqueous phase with a stable water-immiscible volatile organic solvent to form two liquid phases, separating the two phases and vaporizing the organic solvent to recover said high-purity thio acid.

2. A method according to claim 1 wherein said thio acid is O,O-dimethyldithiophosphoric acid.

3. A method according to claim 1 wherein said thio acid is O,O-diethyldithiophosphoric acid.

4. A method according to claim 1 wherein sulfuric or phosphoric acid or an alkali metal salt thereof is added to the water in the first step.

5. A method according to claim 4 wherein said additive is sulfuric acid.

6. A method according to claim 1 wherein said organic solvent in the second step is a chlorinated hydrocarbon, an aromatic hydrocarbon, or an ether which has a boiling point of less than 45° C. at 1 mm Hg and which is immiscible with water.

7. A method according to claim 1 wherein said solvent vaporization is accomplished by means of batch distillation or thin-film evaporation.

* * * * *